(12) United States Patent
Razavi-Shirazi et al.

(10) Patent No.: US 9,334,507 B2
(45) Date of Patent: *May 10, 2016

(54) BIOPROCESSES FOR MAKING BUTANOL

(71) Applicant: Microvi Biotech, Inc., Hayward, CA (US)

(72) Inventors: Fatemeh Razavi-Shirazi, Hayward, CA (US); Ameen Razavi, Fremont, CA (US)

(73) Assignee: MICROVI BIOTECH, INC., Hayward, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 14/106,669

(22) Filed: Dec. 13, 2013

(65) Prior Publication Data

US 2014/0106425 A1 Apr. 17, 2014

Related U.S. Application Data

(63) Continuation-in-part of application No. 13/918,868, filed on Jun. 14, 2013, which is a continuation-in-part of application No. 13/918,838, filed on Jun. 14, 2013.

(60) Provisional application No. 61/689,921, filed on Jun. 15, 2012, provisional application No. 61/689,922, filed on Jun. 15, 2012, provisional application No. 61/689,923, filed on Jun. 15, 2012, provisional application No. 61/689,924, filed on Jun. 15, 2012, provisional application No. 61/689,925, filed on Jun. 15, 2012, provisional application No. 61/689,929, filed on Jun. 15, 2012, provisional application No. 61/689,930, filed on Jun. 15, 2012, provisional application No. 61/689,932, filed on Jun. 15, 2012, provisional application No. 61/689,933, filed on Jun. 15, 2012, provisional application No. 61/689,935, filed on Jun. 15, 2012, provisional application No. 61/689,939, filed on Jun. 15, 2012, provisional application No. 61/689,940, filed on Jun. 15, 2012, provisional application No. 61/689,943, filed on Jun. 15, 2012, provisional application No. 61/689,945, filed on Jun. 15, 2012, provisional application No. 61/689,953, filed on Jun. 15, 2012, provisional application No. 61/849,725, filed on Feb. 1, 2013, provisional application No. 61/850,631, filed on Feb. 20, 2013, provisional application No. 61/851,467, filed on Mar. 8, 2013, provisional application No. 61/852,451, filed on Mar. 15, 2013, provisional application No. 61/689,941, filed on Jun. 15, 2012, provisional application No. 61/689,944, filed on Jun. 15, 2012, provisional application No. 61/689,948, filed on Jun. 15, 2012.

(51) Int. Cl.
*C12P 7/16* (2006.01)
*C12P 7/06* (2006.01)
*C12P 7/28* (2006.01)
*C12N 11/14* (2006.01)
*C12N 11/04* (2006.01)
*C02F 3/34* (2006.01)

(52) U.S. Cl.
CPC . *C12P 7/16* (2013.01); *C12N 11/04* (2013.01); *C12N 11/14* (2013.01); *C12P 7/065* (2013.01); *C12P 7/28* (2013.01); *C02F 3/34* (2013.01); *Y02W 10/37* (2015.05)

(58) Field of Classification Search
None
See application file for complete search history.

(56) References Cited

U.S. PATENT DOCUMENTS

| | | |
|---|---|---|
| 3,767,790 A | 10/1973 | Guttag |
| 4,148,689 A | 4/1979 | Hino et al. |
| 4,195,129 A | 3/1980 | Fukui et al. |
| 4,250,264 A | 2/1981 | Nelson et al. |
| 4,287,305 A | 9/1981 | Compere et al. |
| 4,352,883 A | 10/1982 | Lim |
| 4,450,233 A | 5/1984 | Mimura et al. |
| 4,469,600 A | 9/1984 | Frydman et al. |
| 4,524,137 A | 6/1985 | Hagerdal et al. |
| 4,546,081 A | 10/1985 | Yamada et al. |
| 4,647,536 A | 3/1987 | Mosbach et al. |
| 4,659,664 A | 4/1987 | de Buda |
| 4,727,030 A | 2/1988 | Ishimura et al. |
| 4,774,178 A | 9/1988 | Egerer et al. |
| 4,791,061 A | 12/1988 | Sumino et al. |
| 4,816,399 A | 3/1989 | Lawford |
| 4,921,803 A | 5/1990 | Nohr |
| 4,950,596 A | 8/1990 | Cheng et al. |
| 4,975,375 A | 12/1990 | Haruta et al. |
| 5,034,324 A | 7/1991 | Shinozaki et al. |
| 5,071,747 A | 12/1991 | Hough et al. |
| 5,089,407 A | 2/1992 | Baker et al. |

(Continued)

FOREIGN PATENT DOCUMENTS

JP 10-314782 12/1998

OTHER PUBLICATIONS

Yarris, Lynn, "New Synthetic Biology Technique Boosts Microbial Production of Diesel Fuel," Berkeley Lab, Lawrence Berkeley National Laboratory, 4 pages, Mar. 26, 2012.

(Continued)

*Primary Examiner* — John S Brusca
*Assistant Examiner* — Sharon M Papciak
(74) *Attorney, Agent, or Firm* — Dentons US LLP

(57) ABSTRACT

Butanol is produced by the bioconversion of substrate using a biocatalyst comprising an open, porous hydrophilic polymeric structure having microorganisms for the bioconversion irreversibly retained therein wherein the microorganisms have undergone phenotypic alterations which includes enhanced tolerance to butanol.

25 Claims, 2 Drawing Sheets

(56) References Cited

U.S. PATENT DOCUMENTS

| | | | |
|---|---|---|---|
| 5,100,673 | A | 3/1992 | Bader et al. |
| 5,112,750 | A | 5/1992 | Tanaka et al. |
| 5,137,818 | A | 8/1992 | Harder et al. |
| 5,279,745 | A | 1/1994 | Jeffers et al. |
| 5,290,693 | A | 3/1994 | Chen et al. |
| 5,324,445 | A | 6/1994 | Langley et al. |
| 5,439,859 | A | 8/1995 | Durante et al. |
| 5,462,866 | A | 10/1995 | Wang |
| 5,486,292 | A | 1/1996 | Bair et al. |
| 5,541,234 | A | 7/1996 | Unger et al. |
| 5,595,893 | A | 1/1997 | Pometto, III et al. |
| 5,620,883 | A | 4/1997 | Shao et al. |
| 5,840,338 | A | 11/1998 | Roos et al. |
| 5,906,828 | A | 5/1999 | Cima et al. |
| 6,077,432 | A | 6/2000 | Coppola et al. |
| 6,133,004 | A | 10/2000 | Sato et al. |
| 6,139,963 | A | 10/2000 | Fujii et al. |
| 6,153,416 | A | 11/2000 | Yuan |
| 6,214,619 | B1 | 4/2001 | Sato et al. |
| 6,258,870 | B1 | 7/2001 | Hubbell et al. |
| 6,337,019 | B1 | 1/2002 | Razavi-Shirazi |
| 6,395,521 | B1 | 5/2002 | Miura |
| 6,395,522 | B1 | 5/2002 | DeFilippi et al. |
| 6,610,205 | B2 | 8/2003 | Sato et al. |
| 6,855,513 | B1 | 2/2005 | Whiteley et al. |
| 7,060,185 | B2 | 6/2006 | Kim et al. |
| 7,384,777 | B2 | 6/2008 | Willuweit et al. |
| 7,556,961 | B2 | 7/2009 | Isaka et al. |
| 7,659,105 | B2 | 2/2010 | Burd et al. |
| 7,704,733 | B2 | 4/2010 | Sumino et al. |
| 7,794,590 | B2 | 9/2010 | Yoshikawa et al. |
| 7,816,110 | B2 | 10/2010 | Aoyama et al. |
| 7,842,185 | B2 | 11/2010 | Abe et al. |
| 7,888,062 | B1 | 2/2011 | Garner et al. |
| 7,931,807 | B2 | 4/2011 | Bowman |
| 8,101,808 | B2 | 1/2012 | Evanko et al. |
| 8,227,226 | B2 | 7/2012 | Kitasaki et al. |
| 8,241,890 | B2 | 8/2012 | Stloukal |
| 8,293,510 | B2 | 10/2012 | Detamore et al. |
| 2002/0164364 | A1 | 11/2002 | Quong |
| 2005/0037082 | A1 | 2/2005 | Wan et al. |
| 2005/0269261 | A1 | 12/2005 | Sublette |
| 2008/0044891 | A1 | 2/2008 | Kinley et al. |
| 2009/0061499 | A1 | 3/2009 | Stloukal et al. |
| 2009/0171129 | A1 | 7/2009 | Evanko et al. |
| 2009/0203103 | A1 | 8/2009 | Pierce et al. |
| 2009/0258051 | A1 | 10/2009 | Chidambaram et al. |
| 2009/0258404 | A1 | 10/2009 | Mikkelsen et al. |
| 2010/0105103 | A1 | 4/2010 | Juan et al. |
| 2010/0133114 | A1 | 6/2010 | Bukshpan et al. |
| 2010/0143993 | A1 | 6/2010 | Erdner-Tindall et al. |
| 2010/0230348 | A1 | 9/2010 | Isaka et al. |
| 2010/0233771 | A1 | 9/2010 | McDonald et al. |
| 2010/0330633 | A1 | 12/2010 | Walther et al. |
| 2011/0006000 | A1 | 1/2011 | Post et al. |
| 2011/0039317 | A1 | 2/2011 | Medoff |
| 2011/0053236 | A1 | 3/2011 | Walmsley et al. |
| 2011/0129887 | A1 | 6/2011 | Contag et al. |
| 2011/0152176 | A1 | 6/2011 | Horswill |
| 2011/0186508 | A1 | 8/2011 | Bowman |
| 2011/0233125 | A1 | 9/2011 | Jones et al. |
| 2011/0250660 | A1 | 10/2011 | Liao et al. |
| 2012/0115045 | A1 | 5/2012 | Kapopara et al. |
| 2012/0142531 | A1 | 6/2012 | Mazeaud et al. |
| 2012/0208255 | A1 | 8/2012 | Andersen et al. |
| 2012/0308632 | A1 | 12/2012 | Ghigo et al. |
| 2013/0022578 | A1 | 1/2013 | Newman et al. |
| 2013/0023035 | A1 | 1/2013 | Bielinski et al. |
| 2013/0023053 | A1 | 1/2013 | March et al. |
| 2013/0034907 | A1 | 2/2013 | Collins et al. |
| 2013/0035513 | A1 | 2/2013 | Hu et al. |
| 2013/0149757 | A1 | 6/2013 | Day et al. |

OTHER PUBLICATIONS

Zhang et al., "Nitrate Removal by Thiobacillus Dentrificans Immobilized on Poly(vinyl alcohol) Carriers," Journal of Hazardous Materials (2008), 6 pages.

Zhou et al., "Recent Patents on Immobilized Microorganism Technology and Its Engineering Application in Wastewater Treatment," Recent Patents on Engineering, (2008), vol. 2, pp. 28-35.

Pegasus / Pegazur / Bio-Tube Process, Stowa-Selected Technologies, Jun. 13, 2006, 4 pages.

http://books.google.com/books?id_TheEtoLS8kcC&printsec=frontcover#v=onepage&q=butanol&f=false, "Handbook on Clostridia," 372, 2 pages, Internet citation; document with no date; other information.

http://kurakay-aqua.com.jp/en/product.pvagel.html, "PVA-Gel Bioreactor," Kuraray Aqua Co., Ltd., 3 pages, Internet citation; downloaded Jun. 24, 2014.

MIT Open Access Articles—Nielsen, David R., et al., Predicting the Adsorption of Second Generation Biofuels by Polymeric Resins with Applications for In Situ Product Recovery (ISPR), Bioresource Technology 101.8 (2010), pp. 2762-2769.

Gevo, White Paper, Transportation Fuels, "Renewable Solution: Isobutanol—A Renewable Solution for the Transportation Fuels Value Chain," May 2011, 16 pages.

Rudney, Harry, "Propanediol Phosphate as a Possible Intermediate in the Metabolism of Acetone," Dept. of Biochemistry, School of Med., Western Reserve Univ., Cleveland, OH, Nov. 1953, pp. 361-371.

Berezina, O. V., "Microbial Producers of Butanol," Applied Biochemistry and Microbiology, vol. 48, No. 7, 2012, pp. 625-638.

Kaminski, W., et al., "Biobutanol—Production and Purification Methods," Ecological Chemistry and Engineering S, vol. 18, No. 1, 2011 pp. 31-37.

Millat, T., et al., "The pH-Induced Metabolic Shift from Acidogenesis to Solventogenesis in Clostridium Acetobutylicum—Form Experiments to Models," Experimental Standard Conditions of Enzyme Characterization, Sep. 2011, Germany, pp. 33-53.

Barcina et al., "The Viable But Nonculturable Phenotype: A Crossroads in the Life-Cycle of Non-Differentiating Bacteria?," Rev Environ Sci Biotechnol (2009) vol. 8, pp. 245-255.

Ben-Jacob et al., "Self-Engineering Capabilities of Bacteria," J. R. Soc. Interface, (2006), vol. 3, pp. 197-214.

Chen et al., "Surface hydration: Principles and Applications Toward Low-Fouling/Nonfouling Biomaterials," Polymer 51, (2010), pp. 5283-5293.

Cho et al., "Self-Organization in High-Density Bacterial Colonies: Efficient Crowd Control," PLoS Biology, Nov. 2007, vol. 5, Issue 11, pp. 2614-2623.

Choi et al., "Engineered Materials and the Cellular Microenvironment: A Strengthening Interface Between Cell Biology and Bioengineering," Trends in Cell Biology, Dec. 2010, vol. 20, No. 12, pp. 705-714.

Christensson et al., "ANITA™ Mox-A BioFarm Solution for Fast Start-up of Deammonifying MBBRs," Sweden, WEFTEC. 2011, 18 pages.

Dawson et al., ""Persisters": Survival at the Cellular Level," PLoS Pathogens, Jul. 2011, vol. 7, Issue 7, pp. 1-3.

Delaittre et al., "Chemical Approaches to Synthetic Polymer Surface Biofunctionalization for Targeted Cell Adhesion Using Small Binding Motifs," Soft Matter, 2012, vol. 8, pp. 7323-7347.

Donlan, Rodney M., "Biofilms: Microbial Life on Surfaces," Emerging Infectious Diseases, vol. 8, No. 9, Sep. 2002, pp. 881-890.

Dunlop, Mary J., "Engineering Microbes for Tolerance to Next-Generation Biofuels," Dunlop Biotechnology for Biofuels, 2011, vol. 4, No. 32, pp. 1-9.

Entry et al., "Polyacrylamide Removes Microorganisms and Nutrients from Surface Water," USDA, Northwest Irrigation & Soils Research Lab, Kimberly, ID, 9 pages, Poster presentation; document with no date; other information.

Joshi et al., "Effect of Molecular Weight on Dielectric Properties of Polyvinyl Alcohol Films," J. Appl. Polum. Sci., 102, 2006, pp. 1014-1016.

(56) References Cited

OTHER PUBLICATIONS

Kato et al., "Microbial Interspecies Electron Transfer via Electric Currents Through Conductive Minerals," PNAS Early Edition, pp. 1-5, Approved May 3, 2012.

Katsikogianni et al., "Concise Review of Mechanisms of Bacterial Adhesion to Biomaterials and of Techniques Used in Estimating Bacteria-Material Interactions," Laboratory of Biomechanics and Biomedical Engineering, European Cells and Materials, vol. 8, 2004, pp. 34-57.

Kharkar et al., "Designing Degradable Hydrogels for Orthogonal Control of Cell Microenvironments," Chem. Soc. Rev., (2013), vol. 42, pp. 7335-7372.

Manina et al., "A Single-Cell Perspective on Non-Growing but Metabolically Active (NGMA) Bacteria," Current Topics in Microbiology and Immunology, (2013), 27 pages.

Mukamolova et al., "Adoption of the Transiently Non-Culturable State—a Bacterial Survival Strategy?," Advances in Microbial Physiology, (2003) vol. 47, pp. 65-129.

Nagadomi et al., "Treatment of Aquarium Water by Denitrifying Photosynthetic Bacteria Using Immobilized Polyvinyl Alcohol Beads," Journal of Bioscience and Bioengineering, vol. 87, No. 2, (1999), pp. 189-193.

Pashkuleva et al., "Surface Modification of Starch Based Biomaterials Can Simultaneously Enhance Cell Adhesion and Proliferation and Induce Bioactivity," 18th European Conference on Biomaterials, Oct. 1-4, 2003, Stuttgart, Germany, p. T103.

Quan et al., "Reject Water Treatment by Improvement of Whole Cell Anammox Entrapment Using Polyvinyl Alcohol/Alginate Gel," Biodegradation, Nov. 2011, vol. 22, Issue 6, pp. 1155-1167.

Renner et al., "Physicochemical Regulation of Biofilm Formation," MRS Bulletin, vol. 36, May 2011, pp. 1-9.

Rooke et al., "Novel Photosynthetic CO2 Bioconvertor Based on Green Algae Entrapped in Low-Sodium Silica Gels," J. Mater. Chem., (2011), vol. 21, pp. 951-959.

Sousa et al., "Phenotypic Switching: An Opportunity to Bacteria Thrive," Science against microbial pathogens: communicating current research and technological advances, A. Mendez-Vilas (Ed.), Formatex 2011, pp. 252-262.

Stevens et al., "Exploring and Engineering the Cell Surface Interface," Science, vol. 310, Nov. 18, 2005, pp. 1135-1138.

Stolpovsky et al., "Incorporating Dormancy in Dynamic Microbial Community Models," Ecological Modeling 222 (2011) pp. 3092-3102.

Sun et al., "Optimization of Entrapping Conditions of Nitrigying Bacteria and Selection of Entrapping Agent," 2nd International Conference on Environmental Science and Technology IPCBEE, vol. 6. (2011), pp. V2-414-V2-417.

Tiraferri et al., "Hydrophilic Thin-Film Composite Forward Osmosis Membranes Functionalized with Surface-Tailored Nanoparticles," ACS Appl. Materials and Interfaces (2012) vol. 4, pp. 5044-5053.

Tuson et al., "Bacteria-Surface Interactions," The Royal Society of Chemistry (2013), 13 pages.

Voloshin et al., "The Role of Intercellular Contacts in the Initiation of Growth and in the Development of a Transiently Nonculturable State by Cultures of Rhodococcus rhodochrous Grown in Poor Media," Microbiology, vol. 74, No. 4, (2005) pp. 420-427.

Wong et al., "All together now: Integrating Biofilm Research Across Disciplines," MRS Bulletin, vol. 36, May 2011, pp. 339-342.

BIOPROCESSES FOR MAKING BUTANOL

CROSS-REFERENCE TO RELATED APPLICATIONS

This is a continuation-in-part of U.S. patent application Ser. No. 13/918,868, filed on Jun. 14, 2013, which claims priority to U.S. Provisional Patent Applications No. 61/689,921, filed on Jun. 15, 2012; 61/689,922, filed on Jun. 15, 2012; 61/689,923, filed on Jun. 15, 2012; 61/689,924, filed on Jun. 15, 2012; 61/689,925, filed on Jun. 15, 2012; 61/689,929, filed on Jun. 15, 2012; 61/689,930, filed on Jun. 15, 2012; 61/689,932, fled on Jun. 15, 2012; 61/689,933, filed on Jun. 15, 2012; 61/689,935, filed on Jun. 15, 2012; 61/689,939, filed on Jun. 15, 2012; 61/689,940, filed on Jun. 15, 2012; 61/689,943, filed on Jun. 15, 2012; 61/689,945, filed on Jun. 15, 2012; 61/689,953, filed on Jun. 15, 2012; 61/849,725, filed on Feb. 1, 2013; 61/850,631, filed on Feb. 20, 2013; 61/851,467, filed on Mar. 8, 2013; and 61/852,451, filed on Mar. 15, 2013, and a continuation-in-part of U.S. patent application Ser. No. 13/918,838, filed on Jun. 14, 2013, which claims priority to U.S. Provisional Patent Applications Nos. 61/689,941, 61/689,944 and 61/689,948, filed Jun. 15, 2012, all herein incorporated by reference in their entirety.

STATEMENT REGARDING FEDERALLY SPONSORED RESEARCH OR DEVELOPMENT

None

TECHNICAL FIELD

The bioconversion of substrate to butanol, especially n-butanol (1-butanol) and isobutanol, is well-known. The useful substrates include sugars and syngas. Photosynthetic processes using carbon dioxide as the substrate have also been proposed. Butanol is a chemical with industrial application and has been used as a liquid fuel or fuel additive to petroleum products.

One of the challenges faced in the metabolic production of butanol is its toxicity to, or its inhibitory effect on, microorganisms. Accordingly, the concentration of butanol in fermentation media has to be maintained very low, often below about 2.5 volume percent. This, in turn, increases the costs of separating butanol from water, especially since butanol and water form an azeotrope. Processes involving immiscible extractant have been proposed to recover butanol from the fermentation media to both maintain a sublethal concentration of butanol in the fermentation medium and to reduce the amount of water that has to be removed from the butanol. Considerable efforts have been expended to genetically modify the microorganisms to tolerate greater concentrations of butanol in the fermentation media. Although more tolerant strains have been developed through selection and genetic modification, the concentrations of butanol that can be tolerated by the microorganisms remain very low.

Shirazi, et al., in the above-mentioned U.S. patent application Ser. No. 13/918,868, disclose biocatalysts having a high tolerance to the presence of butanol. These biocatalysts comprise i. a solid structure of hydrated hydrophilic polymer defining an interior structure having a plurality of interconnected major cavities having a smallest dimension of between about 5 and about 100 microns and an HEV of at least about 1000 and ii. a population of microorganisms capable of converting sugars to at least one organic product substantially irreversibly retained in the interior of the solid structure, said population of microorganisms being in a concentration of at least about 60 grams per liter based upon the volume defined by the exterior of the solid structure when fully hydrated.

The microorganisms are believed to undergo phenotypic alterations enabling, inter alia, enhanced tolerance to butanol, including in fermentation media saturated with butanol. The disclosed biocatalysts are particularly attractive for continuous processes for the bioconversion of substrate to butanol as the biocatalyst is substantially devoid of solids generation, and, being a solid, enables separation of the biocatalyst from the fermentation medium. Moreover, the biocatalyst has a long lifetime and competition with undesired microorganism is substantially eliminated. For ease of reference, these biocatalysts are herein referred to as ME biocatalysts.

SUMMARY

In accordance with the processes of this invention, ME biocatalysts are used for the bioconversion of substrate to butanol. The butanol may be one or more isomers of butanol, and preferably comprises at least one of n-butanol and isobutanol. Thus, continuous processes and batch processes involving the reuse of the biocatalyst are facilitated. Also, the surprising tolerance of ME biocatalysts to butanol enable, if desired, high concentrations, even concentrations yielding a separate butanol phase, to be used. Further the ME biocatalyst is characterized by a high cell density per unit volume, which can enhance bioconversion activity per unit volume of bioreactor in comparison to that of free cell fermentation bioreaction systems.

Since the biocatalysts have a tolerance to butanol at above saturation concentrations in an aqueous medium, the ability to recover butanol from the aqueous medium is enhanced. In a preferred aspect of the processes of this invention, the concentration of butanol in the aqueous medium is allowed to be sufficiently high that a separate butanol phase is formed. Phase separation thus yields a butanol phase, which contains dissolved water, and an aqueous phase. Butanol can be recovered from the butanol phase by distillation. Although a lower boiling, butanol/water azeotrope will occur, this azeotrope can be passed back to the fermentation unit operation and thus recycled for recovery.

In its broadest aspects, the processes of this invention for bioconverting substrate to bioproduct comprising butanol with a biocatalyst comprising microorganisms capable of bioconverting said substrate to butanol comprise:

a. contacting said substrate with said biocatalyst under metabolic conditions for a time sufficient to bioconvert at least a portion of said substrate to butanol, and b. recovering butanol, wherein said biocatalyst comprises microorganisms substantially irreversibly retained in a solid structure, said solid structure being composed of hydrated hydrophilic polymer defining an interior structure having a plurality of interconnected major cavities having a smallest dimension of between about 5 and about 100 microns and an HEV of at least about 1000 wherein said microorganisms have a population in the interior structure of at least about 60 grams per liter based upon the volume defined by the exterior of the solid structure when fully hydrated, wherein the microorganisms maintain their population substantially stable.

The contacting between the substrate and the biocatalyst can be in a non-aqueous or aqueous medium. Since the ME biocatalysts are hydrated, it is not essential that the exterior of the ME biocatalysts be aqueous. The non-aqueous medium can be gaseous or liquid. In some aspects of the processes of this invention wherein the contacting is conducted in an aqueous medium, butanol is recovered from said aqueous medium. Preferably, butanol forms a separate liquid phase in the bioreactor assembly.

The substrate used in the processes of this invention can be any suitable substrate. In some embodiments of this invention, the substrate comprises sugar. Other substrates known in the art can alternatively be used such as glycerol, syngas (wherein the substrate comprises at least one of carbon monoxide and a mixture of hydrogen and carbon dioxide) and carbon dioxide where the bioconversion is by photosynthesis.

In one preferred aspect, this invention pertains to continuous processes for the bioconversion of substrate to bioproduct comprising butanol with a biocatalyst comprising microorganisms capable of bioconverting said substrate to butanol, said processes comprising:
  a. continuously supplying said substrate to bioreactor assembly containing an aqueous medium and biocatalyst;
  b. contacting said substrate with said biocatalyst in an aqueous medium wider metabolic conditions for a time sufficient to bioconvert at least a portion of said substrate to butanol to provide a butanol-laden liquid medium,
  c. withdrawing continuously or intermittently a portion of the butanol-laden liquid medium from the bioreactor assembly; and
  d. recovering butanol from said butanol-laden liquid medium,
wherein said biocatalyst comprises microorganisms substantially irreversibly retained in a solid structure, said solid structure being composed of hydrated hydrophilic polymer defining an interior structure having a plurality of interconnected major cavities having a smallest dimension of between about 5 and about 100 microns and an HEV of at least about 1000 wherein said microorganisms have a population in the interior structure of at least about 60 grams per liter based upon the volume defined by the exterior of the solid structure when fully hydrated, wherein the microorganisms maintain their population substantially stable.

In one further preferred embodiment, butanol is recovered from said butanol-laden liquid medium by (i) phase separating to provide a butanol phase and an aqueous phase, (ii) fractionating by distillation said butanol phase to provide a bottoms fraction comprising butanol and a lower-boiling fraction comprising azeotrope of butanol and water, and (iii) passing to said bioreactor assembly at least a portion of the lower-boiling fraction such that a butanol-containing phase exists in the bioreactor assembly, wherein said butanol-laden liquid medium contains two phases.

Yet another preferred aspect of this invention pertains to continuous processes for the bioconversion of substrate to bioproduct using a microorganism capable of such bioconversion wherein the bioproduct is toxic to the microorganism comprising:
  a. continuously supplying substrate and aqueous medium to at least one first bioreactor containing aqueous medium, said at least one first bioreactor having therein biocatalyst, wherein said biocatalyst comprises microorganisms substantially irreversibly retained in a solid structure, said solid structure being composed of hydrated hydrophilic polymer defining an interior structure having a plurality of interconnected major cavities having a smallest dimension of between about 5 and about 100 microns and an HEV of at least about 1000 wherein said microorganisms have a population in the interior structure of at least about 60 grams per liter based upon the volume defined by the exterior of the solid structure when fully hydrated, wherein the microorganisms maintain their population substantially stable;
  b. maintaining said at least one first bioreactor under metabolic conditions and continuously withdrawing a first reactor effluent from said at least one first bioreactor at a rate sufficient to maintain steady-state conditions and provide a hydraulic residence time sufficient to bioconvert a portion of the substrate, said first bioreactor effluent containing unconsumed substrate and bioproduct, wherein the bioconversion activity to said bioproduct in said at least one first bioreactor is at a first rate;
  c. continuously supplying the withdrawn first bioreactor effluent to at least one subsequent bioreactor containing aqueous medium, said at least one subsequent bioreactor having therein biocatalyst, wherein said biocatalyst comprises microorganisms substantially irreversibly retained in a solid structure, said solid structure being composed of hydrated hydrophilic polymer defining an interior structure having a plurality of interconnected major cavities having a smallest dimension of between about 5 and about 100 microns and an HEV of at least about 1000 wherein said microorganisms have a population in the interior structure of at least about 60 grams per liter based upon the volume defined by the exterior of the solid structure when fully hydrated, wherein the microorganisms maintain their population substantially stable;
  d. maintaining said at least one subsequent bioreactor under metabolic conditions and continuously withdrawing a subsequent bioreactor effluent from said at least one subsequent bioreactor at a rate sufficient to maintain steady-state conditions and provide a hydraulic residence time sufficient to bioconvert at least a portion of the substrate, said subsequent bioreactor effluent containing bioproduct, wherein the bioconversion activity to said bioproduct in said at least one subsequent bioreactor is at a second rate which is lower than the first rate;
  e. continuously separating a bioproduct-rich stream from said withdrawn subsequent bioreactor effluent for product recovery and provide a residual aqueous stream; and
  f. continuously recycling at least a portion of the residual aqueous stream to at least one subsequent bioreactor.

In one preferred embodiment, acidogenesis occurs in the at least one first bioreactor and a portion of the substrate is bioconverted to carboxylate anion, and the first reactor effluent contains carboxylate anion, unconsumed substrate and bioproduct, and solventogenesis occurs in the at least one subsequent bioreactor bioconvert at least a portion of the carboxylate anion and unconsumed substrate to bioproduct.

A further aspect of this invention pertains to processes for the bioconversion of substrate to butanol, especially n-butanol by ABE fermentation, where sufficient butanol is present during the fermentation to affect the distribution of metabolites and increase the ratio of butanol to other metabolites. Without wishing to be limited by theory, it is believed that phenotypic alterations of the microorganisms include an ability of the population of microorganisms in the ME biocatalyst to tolerate the presence of butanol. It is further believed that the presence of butanol can result in further phenotypic alterations to microorganisms in the ME biocatalysts and affect the metabolite distribution of the biocatalysts as compared not only to planktonic microorganisms but also with respect to microorganisms in an ME biocatalyst. Preferably, the biocatalyst is subjected to butanol before or at least at the initiation of the use of the biocatalyst for the bioconversion of substrate to butanol. Broadly, this aspect of the invention pertains to processes for bioconverting substrate to bioproduct comprising butanol with a biocatalyst comprising microorganisms capable of bioconverting said substrate to butanol said microorganism being capable of producing other metabolites, comprise:

a. contacting said biocatalyst with butanol in a concentration sufficient to alter the ratio of butanol production to the production of other metabolites in favor of the production of butanol;
b. contacting said substrate with said biocatalyst under metabolic conditions for a time sufficient to bioconvert at least a portion of said substrate to butanol, and
c. recovering butanol, wherein said biocatalyst comprises microorganisms substantially irreversibly retained in a solid structure, said solid structure comprising hydrated hydrophilic polymer defining an interior structure having a plurality of interconnected major cavities having a smallest dimension of between about 5 and about 100 microns and an HEV of at least about 1000 wherein said microorganisms have a population in the interior structure of at least about 60 grams per liter based upon the volume defined by the exterior of the solid structure when fully hydrated, wherein the microorganisms maintain their population substantially stable.

Step (a) is preferably conducted by contacting the biocatalyst with an aqueous solution containing butanol, preferably at a concentration of at least about 3, more preferably at least about 5, mass percent butanol in the aqueous solution. Most preferably, the aqueous solution is saturated with butanol. Preferably, the butanol is n-butanol or isobutanol, most preferably n-butanol.

Although the biocatalyst can be preconditioned by prior contact with butanol, preferably steps (a) and (b) occur at the same time. In some preferred embodiments, step (b) is conducted in an aqueous medium containing the biocatalyst and the concentration of butanol in the aqueous medium is at least about 30 grains per liter, and most preferably is such that a separate liquid phase is formed. In continuous processes falling within this aspect of the invention, a portion of the butanol withdrawn from a bioreactor assembly used in the processes, is recycled to the bioreactor.

This aspect of the invention is particularly attractive for the bioconversion of substrates using microorganisms capable of co-producing ethanol and acetone with n-butanol (ABE fermentation). In such instances, sufficient butanol concentration is provided that the mass ratio of butanol to total acetone and ethanol is increased by at least about 20 percent, preferably at least about 50 percent, as compared to that ratio provided under essentially the same metabolic conditions but in the absence of a preconditioning of the biocatalyst or the presence of a butanol presence at the initiation of the bioconversion.

DETAILED DESCRIPTION

Figure 1:
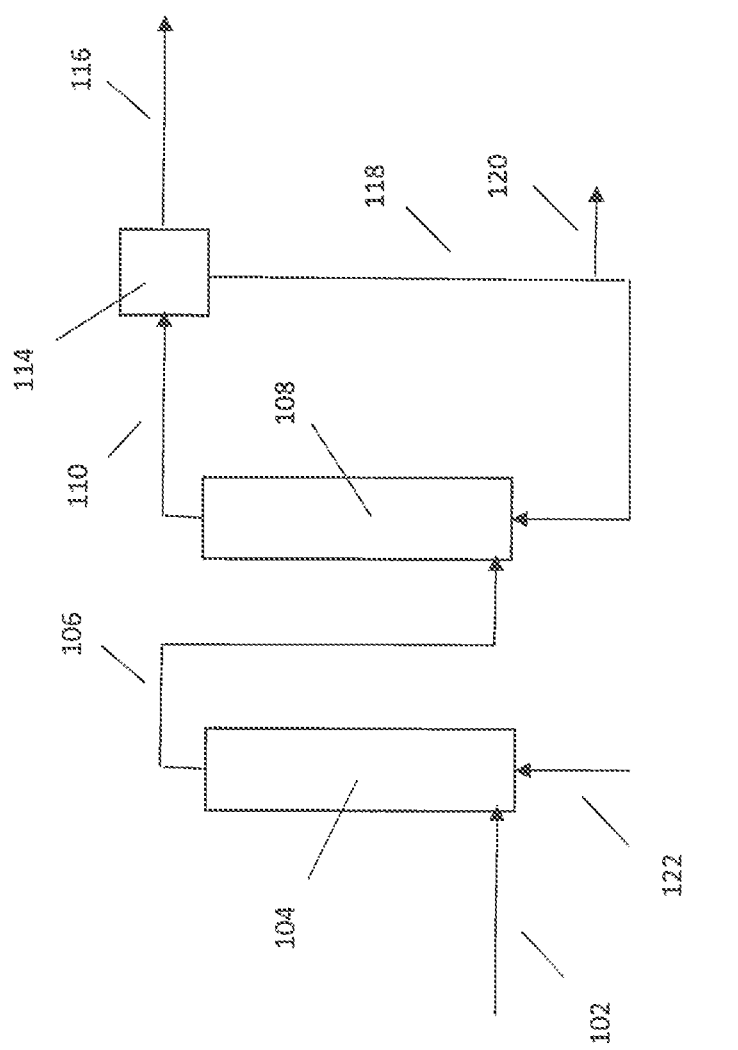
FIG. 1 is a schematic depiction of an apparatus useful in the practice of processes of this invention.

All patents, published patent applications and articles referenced herein are hereby incorporated by reference in their entirety.

DEFINITIONS

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

Acidogenesis and solventogeneis have the meanings set forth in Millat, et al., "The pH-induced Metabolic Shift from Acidogenesis to Solventogenesis in *Clostridium acetobutylicum—from Experiments to Models*", pages 33 to 53 of the published papers from Beilstein-Institut, Experimental Standard Conditions of Enzyme Characterization, Sep. 12-16, 2011, Rüdesheim/Rein, Germany, (http://www.beilstein-institut.de/escec2011/Proceedings/Millat.pdf).

Adhering to the solid structure of the biocatalyst means that the microorganisms are located in cavities in the interior of the biocatalyst and are substantially irreversibly retained therein although extraordinary conditions and treatments (i.e., not normal metabolic conditions for bioconversion using the microorganisms) might be able in some instances to cause the microorganism to exit the biocatalyst. Adhering includes surface attachment to the polymer forming the walls of the catalyst as well as where the retained microorganisms are proximate to a polymeric surface, e.g., within about 10 or about 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Bioconversion activity is the rate of consumption of substrate per hour per gram (wet) of microorganism. Where an increase or decrease in bioconversion activity is referenced herein, such increase or decrease is ascertained under similar metabolic conditions including concentration of substrate and product in the aqueous medium, Bioconversion activity to bioproduct is the rate of production of the bioproduct per hour per gram of microorganism.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms, in some instances, the biofilm extends in a random, three dimensional manner, and the thickness is determined as the maximum, straight line distance between the distal ends. A thin biofilm is a biofilm which does not exceed about 10 microns in any given direction.

A bioreactor assembly is an assembly of one or more vessels suitable to contain water-insoluble liquid and ME biocatalyst and can contain associated equipment such as injectors, recycle loops, agitators, and the like.

A state of essential stasis means that a microorganism population has undergone a substantial cessation of metabolic bioconversion activity but can be revived. The existence of an essential stasis condition can be ascertained by measuring bioconversion activity. The essential stasis condition may be aerobic, anoxic or anaerobic which may or may not be the same as that of normal operating conditions for the microorganism. Where stasis is sought, the temperature is typically in the range of about 0° C. to about 25° C., say, about 4° C. to about 15° C., which may be different from the temperatures used at normal operating conditions.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5 micron and may be as large as about 5 or about 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 and about 10 microns.

Fermentable sugars are sugars that are capable of being bioconverted by microorganisms in the biocatalyst to ethanol and carbon dioxide and may in addition produce other metabolites. For instance, if the microorganism is common yeast, C5 (five carbon) sugars are substantially not fermentable but C6 (six carbon) sugars can be fermented and thus are fermentable sugars.

Fully hydrated means that a biocatalyst is immersed in water at about 25° C. until no further expansion of the superficial volume of the biocatalyst is perceived.

The "Hydration Expansion Volume" (HEV) fir a biocatalyst is determined by hydrating the biocatalyst in water at about 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at about 25° C. for a time sufficient that the volume of the biocatalyst has stabilized and then measuring the superficial volume of the biocatalyst ($V_s$).

The HEV in volume percent is calculated as the amount of $[V_w/V_s] \times 100\%$. To assure dehydration with the ethanol, either a large volume ratio of ethanol to biocatalyst is used or successive immersions of the biocatalyst in fresh ethanol are used. The ethanol is initially dehydrated ethanol.

Irreversibly retained and substantially irreversibly retained mean that the microorganisms are adhering to polymeric structures defining open, porous cavities. Irreversibly retained microorganisms do not include microorganisms located on the exterior surface of a biocatalyst. A microorganisms is irreversibly retained even if the biocatalyst has exterior pores of sufficient size to permit egress of the microorganisms.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

A matrix is an open, porous, polymeric structure and is an article of manufacture having an interconnected plurality of channels or cavities (herein "major cavities") defined by polymeric structures, said cavities being between about 5 and about 100 microns in the smallest dimension (excluding any microorganisms contained therein), wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or about 10 to about 70 or about 100 microns in the smallest dimension (excluding any microorganism contained therein) have nominal major dimensions of less than about 300, preferably less than about 200, microns, and sometimes a smallest dimension of at least about 10 microns. The term open, porous thus refers to the existence of channels or cavities that are interconnected by openings there between.

Metabolic conditions include conditions of temperature, pressure, oxygenation (oxidation reduction potential (ORP)), pH, and nutrients (including micronutrients) and additives required or desired for the microorganisms in the biocatalyst. Nutrients and additives include growth promoters, buffers, antibiotics, vitamins, minerals, nitrogen sources, and sulfur sources and carbon sources where not otherwise provided.

Permeable means that a component can enter or exit the major cavities from or to the exterior of the biocatalyst.

A phenotypic change or alteration or phenotypic shift is a change in a microorganism's traits or characteristics from environmental factors and is thus different from a change in the genetic make-up of the microorganism.

Population of microorganisms refers to the number of microorganisms in a given volume and include substantially pure cultures and mixed cultures.

Quiescent means that the aqueous medium in a biocatalyst is still; however, flows of nutrients and substrates and bioproducts can occur through the aqueous medium via diffusion and capillary flow.

Retained solids means that solids are retained in the interior of the biocatalyst. The solids may be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

A stable population of microorganisms means that the population of microorganisms does not decrease by more than about 50 percent nor increase by more than about 400 percent.

Substrates are carbon sources, electron donors, electron acceptors and other chemicals that can be metabolized by a microorganism, which chemicals may or may not provide sustaining value to the microorganism.

Sugar means carbohydrates having 5 to 12 carbon atoms and includes, but is not limited to, D-glyceraldehyde, L-glyceraldehyde, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, D-mannose, L-mannose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEHU).

Syngas means at least one of (i) carbon monoxide and (ii) a mixture of hydrogen and carbon dioxide.

Typical Bioreactor Systems are those operated on a continuous, semi-continuous or batch mode of operation and include bioreactor designs such as, but are not limited to, ponds (in the case of photosynthetic processes), bubble column reactors, stirred reactors, packed bed reactors, trickle bed reactors, fluidized bed reactors, plug flow (tubular) reactors, and membrane (biofilm) reactors. In conducting photosynthetic bioconversions, the reactors may be designed to permit the transfer of photo energy. The biocatalyst may be freely mobile in the aqueous medium or fixed, e.g., to a structure in the reactor vessel, or may itself provide a fixed structure. More than one reactor vessel may be used. For instance, reactor vessels may be in parallel or in sequential flow series.

Typical Mesophilic Conditions are metabolic conditions that include a temperature in the range of between about 0° C. and about 50° C. or more depending upon the temperature tolerance of the microorganism, most frequently, about 5° C. or about 10° C. to about 40° C. or about 45° C.; a pressure in the ranges from about 70 to about 500, say, about 90 to about 300, kPa absolute due to equipment configurations although higher and lower pressures could find applicability; and a pH in the range of between about 3 and about 9. The Typical Mesophilic Conditions can be aerobic or anaerobic.

Typical Separation Techniques for chemical products include phase separation for gaseous chemical products, the use of a still, a distillation column, phase separation (liquid-liquid and solid-liquid), gas stripping, flow-through centrifuge, Karr column for liquid-liquid extraction, mixer-settler, or expanded bed adsorption. Separation and purification steps may proceed by any of a number of approaches combining various methodologies, which may include centrifugation, filtration, reduced pressure evaporation, liquid/liquid phase separation, membranes, distillation, and/or other methodologies recited herein. Principles and details of standard separation and purification steps are known in the art, for example in "Bioseparations Science and Engineering," Roger G. Harrison et al., Oxford University Press (2003), and Membrane Separations in the Recovery of Biofuels and Biochemicals— An Update Review, Stephen A. Leeper, pp. 99-194, in Separation and Purification Technology, Norman N. Li and Joseph M. Cabo, Eds., Marcel Dekker (1992).

The wet weight or wet mass of cells is the mass of cells from which free water has been removed, i.e., are at the point of incipient wetness. All references to mass of cells is calculated on the basis of the wet mass of the cells.

References to organic acids herein shall be deemed to include corresponding salts and esters.

References to matrix dimensions and volumes herein are of fully hydrated matrices unless otherwise stated or clear from the context.

Process Description

The processes of this invention use ME biocatalysts for the bioconversion of substrate to butanol. The processes may be batch, semi-continuous or, preferably continuous. Substrates may be one or more of normally a gas, liquid or solid. The substrates may be dissolved or in a colloidal dispersion in a liquid medium or be in a gas when contacting the ME biocatalyst. The liquid medium can be aqueous or non-aqueous, including, but not limited to, water-immiscible and water-insoluble, Especially where syngas is the substrate, a non-aqueous liquid medium may be desirable to enhance mass transfer.

The bioconversion processes using the ME biocatalysts may be conducted in any suitable manner employing metabolic conditions sufficient for the biocatalyst to convert the substrate to the sought bioproduct. In a bioreactor assembly more than one type of microorganism can be used, say, by using different biocatalysts, each retaining a different microorganism, or by including more than one microorganism in a biocatalyst. In the processes of this invention, certain metabolic conditions are defined by the surrounding water-insoluble liquid and others are defined by the environment in the interior of the ME biocatalyst, Metabolic conditions broadly include conditions of temperature, pressure, oxygenation, pH, and nutrients (including micronutrients) and additives required or desired for the microorganisms. The hydration of the interior of the ME biocatalysts provides the environment for the microorganisms and thus will define conditions such as pH, oxidation reduction potential and nutrients. Due to the microenvironments and phenotypic alterations associated with the ME biocatalysts, often a broader range of metabolic conditions can be effectively used, and a broader range of conditions in the interior of the ME biocatalyst tolerated than those suitable for planktonic microorganisms.

The metabolic conditions used are those suitable for the microorganisms and the bioconversion. As stated above, the useful range of metabolic conditions are typically broader than those for planktonic bioconversion systems. In general, a microorganism can fall into the categories of psychrophile (optimal growth at about −10° C. to about 25° C.), a mesophile (optimal growth at about 20-about 50° C.), a thermophile (optimal growth about 45° C. to about 80° C.), or a hyperthermophile (optimal growth at about 80° C. to about 100° C.). Many microorganisms are mesophiles and Typical Mesophilic Conditions are typically preferred.

Any suitable bioreactor assembly may be used including Typical Bioreactor Systems. The bioreactor may or may not be sterilized prior to introducing the aqueous medium. Due to the use of biocatalysts containing significant populations of microorganisms, bioreactors can have a rapid start-up time. The high cell densities together with the enhanced bioconversion rate provide for high conversion efficiencies of substrate with relatively brief average residence times in the bioreactor. The duration of contact between the water-insoluble liquid and the ME biocatalyst in the bioreactor assembly is sufficient to achieve a sought conversion of substrate to bioproduct. Both mass transfer and biocatalytic rates are factors in determining the duration of contact.

The bioproduct may be recovered from the aqueous medium in any suitable manner including the Typical Separation Techniques. In preferred aspects of the processes of this invention, the bioreactor assembly contains an aqueous medium and butanol is present in an amount sufficient to form a separate liquid phase. As stated above, recovery of butanol from the separate liquid phase, even though the phase contains water, is more advantageous than recovery of butanol from the aqueous phase. The recovery may be by any Typical Separation Technique; however, fractionation by distillation is a preferred unit operation where a separate butanol phase exists.

The processes of this invention are particularly attractive for integration with bioethanol plants especially where a separate butanol phase exists in the bioreactor assembly and can be phase separated from the aqueous phase. The aqueous phase, for instance where n-butanol is produced, can be passed to the distillation unit operation of the ethanol plant which is adapted to recover fusel oils. Since the ME biocatalyst irreversibly retains the microorganisms, the microorganisms used for the bioconversion to produce butanol are not introduced into the ethanol process stream.

Where the substrate is sugar and is provided in an aqueous medium to the bioreactor assembly, in some instances it may be desired to evaporate a portion of the water, which can be done at less energy consumption than the distillation of butanol from water, and admix the concentrated stream with a butanol containing liquid, including, but not limited to, a butanol phase from decanting a butanol-containing fermentation product and butanol/water azeotrope. In these instances, the mass ratio of butanol to substrate is sometimes in the range of about 0.1:1 to about 10:1.

Microorganisms

The microorganisms may be unicellular or may be multicellular that behaves as a single cell microorganism such as filamentous growth microorganisms and budding growth microorganisms. Often the cells of multicellular microorganisms have the capability to exist singularly. The microorganisms can be of any type, including, but not limited to, those microorganisms that are aerobes, anaerobes, facultative anaerobes, heterotrophs, autotrophs, photoautotrophs, photoheterotrophs, chemoautotrophs, and/or chemoheterotrophs. The cellular activity, including cell growth can be aerobic, microaerophilic, or anaerobic. The cells can be in any phase of growth, including lag, (or conduction), exponential, transition, stationary, death, dormant, vegetative, sporulating, etc. The one or more microorganisms be a psychrophile (optimal growth at about $-10°$ C. to about $25°$ C.), a mesophile (optimal growth at about 20-about $50°$ C.), a thermophile (optimal growth about $45°$ C. to about $80°$ C.), or a hyperthermophile (optimal growth at about $80°$ C. to about $100°$ C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant microorganism (including, but not limited to genetically engineered microorganisms). A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme), Sought properties in wild-type or genetically modified microorganisms can often be enhanced through a natural modification process, or self-engineering process, involving multigenerational selective harvesting to obtain strain improvements such as microorganisms that exhibit enhanced properties such as robustness in an environment or bioactivity. See, for instance, Ben-Jacob, et al., Self-engineering capabilities of bacteria, J. R. Soc. Interface 2006, 3, doi: 10.1098/rsif.2005.0089, 22 Feb. 2006.

Examples of microorganisms capable to producing butanol are butyrogens and include, but are not limited to, wild-type or recombinant *Clostridia*, such as *C. acetobutylicum*, *C. beijerinckii*, *C. pasteurianum*, *saccharobutylicum*, *C. saccharoperbutylacetonicum*; *Oeneococcus oeni*; and *Ralstonia eutropha*, and recombinant microorganisms such as *E. coli* and *Saccharomyces cerevisiae* into which pathways for making butanol have been added. See, for instance, United States Published Patent Application No. 2010/0143993 for a more extensive discussion of other microorganisms for making butanol. Genetically enhanced photoautotrophic cyanobacteria, algae, and other photoautotrophic organisms have been adapted to bioconvert carbohydrates internal to the microorganism directly to butanol. For example, genetically modified cyanobacteria having constructs comprising DNA fragments encoding pyruvate decarboxylase (pdc) and alcohol dehydrogenase (adh) enzymes are described in U.S. Pat. No. 6,699,696.

ME Biocatalyst

A. ME Biocatalyst Overview

The ME biocatalysts have a polymeric structure (matrix) defining interconnected major cavities, i.e., are open, porous matrices, in which the microorganisms are metabolically retained in the interior of the matrices, that is, the microorganisms promote the adherence rather than being physically restrained by an external structure. In the ME biocatalysts, the microorganisms and their communities, inter alia, regulate their population. Also, in conjunction with the sensed nature of the microenvironment in the matrices, it is believed that the microorganisms establish a spatial relationship among the members of the community.

The community communication among the microorganisms and the behavior of the microorganisms thus are important to achieving and maintaining the metabolically retained microorganisms. The communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated, which are believed to commence during the formation of the biocatalysts, and phenotypic shifts occur to enable the metabolic retention and modulate the population of microorganisms.

The environment to achieve the metabolically-retained, stable population of microorganisms is characterized by a highly hydrated structure of hydrophilic polymer, which structure defines a plurality of interconnected cavities of between about 5 and about 100 microns in the smallest dimension and has a Hydration Expansion Volume (HEV) of at least about 1000. The structure thus defines the microenvironments for the microorganisms. These microenvironments not only facilitate communication among the microorganisms but also in some instances modulate the environmental stresses on the microorganisms and modulate the supply of substrate and nutrients to the microorganisms. The highly hydrated and expanded structure of the porous matrices and its openness also can accommodate the metabolic retention of a large population of microorganisms and accommodate community behaviors associated with the metabolic retention.

The microorganisms that are retained in the matrices have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The ME biocatalysts have a substantial absence of biofilms in their interiors that are larger than thin biofilms. Hence, any biofilms that may ultimately form in the biocatalysts are relatively thin, e.g., up to about 10, and preferably up to about 2 or about 5, microns in thickness, and stable in size. Thus, each thin biofilm is often only a few cells and is connected in an exo-network.

The communications are believed to result in the community of microorganisms maintaining a relatively constant population in the interior of the biocatalyst. Another phenotypic alteration occurring in the ME biocatalysts, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus the population of microorganisms in a biocatalyst of this invention may have microorganisms adapting to different circumstances but yet working in unison for the benefit of the community.

In some instances the porous matrix may provide modulation of the substrate and nutrients to the microorganisms to optimize metabolic pathways involving substrates that are available, and these pathways may or may not be the primarily used pathways where ample substrate and other nutrients are available. Accordingly, microorganisms in the biocatalysts may exhibit enhanced bioactivity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The biocatalysts exhibit an increased tolerance to toxins. In some instances, communications among microorganisms and any exo-network may facilitate the population establishing defenses against toxins. The community response to the presence of toxins has been observed in the ME biocatalysts.

In summary, due to the microenvironments in the ME biocatalyst, communication among the microorganisms and the phenotypic alterations undergone by the microorganisms, the biocatalysts provide a number of process-related advantages including, but not limited to, no solid debris being generated,
the potential for high densities of microorganisms in a bioreactor,
stable population of microorganisms and bioactivity over extended periods of time,
metabolic shift of microorganisms towards production rather than growth and carbon flow shift,
ability of microorganisms to undergo essential stasis for extended durations,
ability to quickly respond to changes in substrate rate of supply and concentration,
attenuation of diauxic growth,
enhanced control and modulation of pH and redox balances in the microenvironment of the biocatalyst,
greater tolerance to substrate, bioproduct and contaminants,
ability to bioconvert substrate at ultralow concentrations,
ability to use slower growing and less robust microorganisms and increased resistance to competitiveness,
enhanced microorganism strain purity capabilities
ability to be subjected to in situ antimicrobial treatment,
ability to quickly start a bioreactor since the density of microorganism required at full operation is contained in the biocatalyst,
ability to contact biocatalyst with gas phase substrate, and
ease of separation of bioproduct from biocatalyst thereby facilitating continuous operations.

If desired, the biocatalysts may be treated to enhance the formation of the exo-network, and if desired, thin biofilms, prior to use in the metabolic process. However, performance of the biocatalyst is not generally dependent upon the extent of exo-network formation, and often bioconversion activities remain relatively unchanged between the time before the microorganisms have attached to the polymeric structure and the time when extensive exo-network structures have been generated.

B. Physical Description of the Porous Matrices

The ME biocatalysts comprise a matrix having open, porous interior structure with microorganisms irreversibly, metabolically retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads, which may be spherical, oblong, or freeform. The matrices, whether self-supporting or placed on or in a preformed structure, preferably have a thickness or axial dimension of less than about 5, preferably less than about 2, say, between about 0.01 to about 1, centimeter(s).

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The ME biocatalyst has major cavities, that is, open, interconnected regions of between about 5 or about 10 to about 70 or about 100 microns in the smallest dimension (excluding any microorganisms contained therein). For the purposes of ascertaining dimensions, the dimensions of the microorganisms include any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to about 20, e.g., about 1 to about 5 or about 10, microns. The cumulative volume of major cavities, excluding the volume occupied by microorganisms and mass associated with the microorganisms, to the volume of the biocatalyst is generally in the range of about 40 or about 50 to about 70 or about 99, volume percent. In many instances, the major cavities constitute less than about 70 percent of the volume of the fully hydrated catalyst with the remainder constituting the smaller channels and pores. The volume fraction of the biocatalyst that constitutes the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The ME biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of about 90 to about 99 or more, percent. Preferably, the biocatalyst exhibits a Hydration Expansion Volume (HEV) of at least about 1000, frequently at least about 5000, preferably at least about 20,000, and sometimes between about 50,000 and about 200,000, percent.

Usually, the type of polymer selected and the void volume percent of the matrices are such that the matrices have adequate strength to enable handling, storage and use in a bioconversion process.

The porous matrices may or may not have an exterior skin. Preferably, the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and about 10, preferably about 2 to about 7, microns in average diameter. The pores may comprise about 1 to about 30, say, about 2 to about 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or about 3 microns. Where a skin is present, its thickness is usually less than about 50, say, between about 1 and about 25, microns. It should be understood that the thickness of the skin can be difficult to discern where the porous matrix has an anisotropic structure with the densest structure being at the exterior of the matrix.

A high density of microorganisms can exist at steady-state operation within the biocatalysts. The combination of the flow channels and the high permeability of the polymeric structure defining the channels enable viable microorganism population throughout the matrix, albeit with a plurality of unique microenvironments and nano-environments. In some instances, the cell density based upon the volume of the biocatalyst is preferably at least about 100 grams per liter, preferably at least about 150 or about 200, and often between about 250 and about 750, grams per liter.

Enzyme-Containing ME Biocatalysts

In another aspect, the ME biocatalysts can contain, in addition to the microorganisms, one or more extracellular enzymes in the interior of the biocatalyst cause a catalytic change to a component which may be substrate or other nutrients, or a bioproduct or by-product or co-product of the microorganisms, or may be a toxin, phage or the like. Typically extracellular enzymes bond or adhere to solid surfaces, such as the hydrophilic polymer, solid additives, cell walls and extracellular polymeric substance. Hence, the enzymes can be substantially irreversibly retained in the interior of the biocatalyst. Due to the structure of the ME biocatalysts, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

Representative enzymes especially for breaking down carbohydrates include, without limitation: cellulose, including one or more enzymes in the classes of endo-glucanases, exoglucanases, and β-glucosidases; endo-1,4-β-D-xylanases; exo-1,4-β-D-xylosidases, endo-1,4-β-D-mannanases; β-mannosidases; acetyl xylan esterases; α-glucuronidases; α-L-arabinofuranosidases; α-galactosidases; laccase; manganese peroxidase; lignin peroxidase; pectin methyl esterase; pectate lyase; polygalacturonase; rhamnoglacturonan lysase; glucuronidase; ferulic acid esterase; α-glaactosidase; p-coumaric acid esterase and cellobiohydrolase (e.g., CBHI, CBHII). The enzymes include those described by Heinzelman et al. (2009) *PNAS* 106: 5610-5615, herein incorporated by reference in its entirety.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmam, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

Solid Sorbent-Containing Biocatalysts

The ME biocatalysts may contain one or more particulate solids which can be used to provide a sought density of the ME biocatalyst. The solid, if desired, may be a solid sorbent. The solid sorbent may be the hydrophilic polymer forming the structure or may be a particulate, i.e., a distinct solid structure regardless of shape) contained in the solid structure. The sorbent may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent.

The particulate solid sorbents are preferably nano materials having a major dimension less than about 5 microns, preferably, between about 5 nanometers to about 3 microns. Where the solid sorbent is composed of polymer, the solid structure may be essentially entirely composed of the polymer or may be a block copolymer or polymeric mixture constituting between about 5 and about 90 mass percent of the solid structure (excluding water). Where the solid sorbent is a separate particulate in the biocatalyst, the biocatalyst may comprise between about 5 to about 90 mass percent of the mass of the biocatalyst (excluding water and microorganisms but including both the hydrophilic polymer and the particulates). More than one solid sorbent may be used in a biocatalyst. Preferably the solid sorbent is relatively uniformly dispersed throughout the interior of the biocatalyst although the solid sorbent may have a varying distribution within the biocatalyst. Where the distribution varies, the regions with the higher concentration of solid sorbent often are found toward the surface of the biocatalyst.

Where a particulate sorbent is used, the sorbent comprises an organic or inorganic material having the sought sorptive capacity. Examples of solid sorbents include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to about 2 nanometers in effective diameter.

The solid sorbent may be incorporated into the polymeric structure in any convenient manner, preferably during the preparation of the ME biocatalyst.

Phosphorescent Biocatalysts

The ME biocatalysts may optionally contain phosphorescent material and photosynthetic microorganisms, i.e., microorganisms that uses light energy in a metabolic process. Preferably, the microorganism is an algae, most preferably a microalgae, or cyanobacteria.

The bioactivity of photosynthetic microorganisms can be enhanced to produce expressed bioproduct using broad-based light source such as sunlight. In accordance with the invention, the photosynthetic microorganisms are irreversibly retained in biocatalysts in which the interior of the biocatalyst contains phosphorescent material capable of shifting UV light to light having a wavelength of between about 400 and about 800, preferably between about 450 and about 650, nm and is capable of exhibiting persistence, with the emission of the light often lasting for at least about 5 seconds. A phosphorescent material is a material that has the ability to be excited by electromagnetic radiation into an excited state, but the stored energy is released gradually. Emissions from phosphorescent materials have persistence, that is, emissions from such materials can last for seconds, minutes or even hours after the excitation source is removed. A luminescent material is a material capable of emitting electromagnetic radiation after being excited into an excited state. Persistence is the time it takes, after discontinuing irradiation, for photoluminescent emissions emanating from a photoluminescent object to decrease to the threshold detectability.

The persistence of the radiation enables the microorganisms to be cycled in and out of a region of the culture liquid exposed to the light source and still be productive. With longer persistence durations, the photosynthetic microorganisms can continue photo-bioconversion in the absence of or reduction in light intensity. The ability of the biocatalysts to maintain photosynthetic activity over extended periods of time, often at least about 30 days, and in some instances for at least one year, the cost of the phosphorescent materials is often offset by the increased production, reduced footprint of the bioreactor, and facilitated bioproduct recovery.

The biocatalyst, being highly hydrated is a significant distributor of light radiation to photosynthetic microorganisms retained in the interior of the biocatalyst and also serves to protect the microorganism from photorespiration. The solid debris in the culture liquid (an aqueous solution comprising nutrients for metabolic processes) can be materially reduced, if not essentially eliminated, due to the microorganisms being irreversibly retained in the biocatalyst. Thus, the turbidity is reduced and a given light intensity can thus be found at a greater depth in the culture liquid. These advantages provided by the ME biocatalysts can be realized in any photosynthetic process regardless of whether or not a phosphorescent material is used.

Examples of phosphorescent materials include, but are not limited to, phosphorescent materials are metal sulfide phosphors such as ZnCdS:Cu:Al, ZnCdS:Ag:Al, ZnS:Ag:Al, ZnS:Cu:Al as described in U.S. Pat. No. 3,595,804 and metal sulfides that are co-activated with rare earth elements such as those describe in U.S. Pat. No. 3,957,678. Phosphors that are higher in luminous intensity and longer in luminous persistence than the metal sulfide pigments include compositions comprising a host material that is generally an alkaline earth aluminate, or an alkaline earth silicate. The host materials generally comprise Europium as an activator and often comprise one or more co-activators such as elements of the Lanthanide series (e.g. lanthanum, cerium, praseodymium, neodymium, samarium, gadolinium, terbium, dysprosium, holmium, erbium, thulium, ytterbium, and lutetium), tin, manganese, yttrium, or bismuth. Examples of such phosphors are described in U.S. Pat. No. 5,424,006.

High emission intensity and persistence phosphorescent materials can be alkaline earth aluminate oxides having the formula $MO_mAl_2O_3:Eu^{2+}, R^{3+}$ wherein m is a number ranging from about 1.6 to about 2.2, M is an alkaline earth metal (strontium, calcium or barium), $Eu^{2+}$ is an activator, and R is one or more trivalent rare earth materials of the lanthanide series (e.g., lanthanum, cerium, praseodymium, neodymium, samarium, gadolinium, terbium, dysprosium, holmium, erbium, thulium, ytterbium, lutetium), yttrium or bismuth co-activators. Examples of such phosphors are described in U.S. Pat. No. 6,117,362. Phosphorescent materials also include alkaline earth aluminate oxides having the formula $M_kAl_2O_4:2xEu^{2+}, 2yR^{3+}$ wherein k=1−2x−2y, x is a number ranging from about 0.0001 to about 0.05, y is a number ranging from about x to about 3x, M is an alkaline earth metal (strontium, calcium or barium), $Eu^{2+}$ is an activator, and R is one or more trivalent rare earth materials (e.g. lanthanum, cerium, praseodymium, neodymium, samarium, gadolinium, terbium, dysprosium, holmium, erbium, thulium, ytterbium, lutetium), yttrium or bismuth co-activators. See U.S. Pat. No. 6,267,911B1.

Phosphorescent materials also include those in which a portion of the $Al^{3+}$ in the host matrix is replaced with divalent ions such as $Mg^{2+}$ or $Zn^{2+}$ and those in which the alkaline earth metal ion ($M^{2+}$) is replaced with a monovalent alkali metal ion such as $Li^+$, $Na^+$, $K^+$, $Cs^+$ or $Rb^+$ such as described in U.S. Pat. Nos. 6,117,362 and 6,267,911B1.

High intensity and high persistence silicates have been disclosed in U.S. Pat. No. 5,839,718, such as Sr.BaO.Mg.MO.SiGe:Eu:Ln wherein M is beryllium, zinc or cadmium and Ln is chosen from the group consisting of the rare earth materials, the group 3A elements, scandium, titanium, vanadium, chromium, manganese, yttrium, zirconium, niobium, molybdenum, hafnium, tantalum, tungsten, indium, thallium, phosphorous, arsenic, antimony, bismuth, tin, and lead. Particularly useful are dysprosium, neodymium, thulium, tin, indium, and bismuth. X in these compounds is at least one halide atom.

Other phosphorescent materials include alkaline earth aluminates of the formula $MO.Al_2O_3.B_2O_3:R$ wherein M is a combination of more than one alkaline earth metal (strontium, calcium or barium or combinations thereof) and R is a combination of $Eu^{2+}$ activator, and at least one trivalent rare earth material co-activator, (e.g. lanthanum, cerium, praseodymium, neodymium, samarium, gadolinium, terbium, dysprosium, holmium, erbium, thulium, ytterbium, lutetium), bismuth or manganese. Examples of such phosphors can be found in U.S. Pat. No. 5,885,483. Alkaline earth aluminates of the type $MAl_2O_4$, which are described in U.S. Pat. No. 5,424,006, may also find application as may phosphorescent materials comprising a donor system and an acceptor system such as described in U.S. Pat. No. 6,953,536 B2.

As can be appreciated, many other phosphors can find application. See, for instance, Yen and Weber, Inorganic Phosphors: Compositions, Preparation and Optical Properties, CRC Press, 2004.

The phosphorescent material may be a discrete particle or may be a particle having a coating to facilitate incorporation and retention in the polymer forming the matrix. The particles may be of any suitable shape. Generally the maximum dimension of the of the particles is less than about 1 millimeter, preferably less than about 0.1 millimeter. The particles may be nanoparticles.

The persistence time exhibited by the phosphorescent materials can range from a short duration, e.g., about 5 to about 10 seconds, to as much as about 10 or about 20 hours or more and will be dependent upon the phosphorescent material used. Preferred phosphorescent materials exhibit a persistence of at least about one minute. The intensity of the emitted radiation will, in part, depend upon the concentration of the phosphorescent material in the biocatalyst and the nature of the phosphorescent material. Typically the phosphorescent material is provided in an amount of at least about 0.1, say, between about 0.2 and about 5 or about 10, mass percent of the polymer (non-hydrated) in the biocatalyst. One or more phosphorescent materials may be used in the biocatalyst. Where more than one phosphorescent material are used, the combination may be selected to provide one or more of wave shifting from different light wavelengths contained in the band width of the radiation source and providing differing persistence times. In preferred embodiments the phosphorescent materials are in the form of nanoparticles, e.g., having a major dimension of between about 10 nm and about 10 µm. In some instances, it may be desired to coat the phosphorescent materials with a compatibilizing agent to facilitate incorporation of the phosphorescent material within the polymer. Compatibilizing agents include, but are not limited to, molecules having one or more of hydroxyl, thiol, silyl, carboxyl, or phosphoryl groups.

C. Methods for Making ME Biocatalysts

The components, including microorganisms, used to make the ME biocatalysts and the process conditions used for the preparation of the biocatalysts are not critical to the broad aspects of this invention and may vary widely as is well understood in the art once understanding the principles of metabolically retaining microorganisms described above. In any event, the components and process conditions for making the ME biocatalysts with the irreversibly, metabolically retained microorganisms should not unduly adversely affect the microorganisms.

The ME biocatalysts may be prepared from a liquid medium containing the microorganism and solubilized precursor for the hydrophilic polymer which may be one or more of a polymerizable car solidifiable component or a solid that is fusible or bondable to form the matrix. Aqueous media are most often used due to the compatibility of most microorganisms and enzymes with water. However, with microorganisms that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the microorganism may be suspended in a dispersed, aqueous phase and the polymerizable or solidifiable component may be contained in a continuous solvent phase.

The liquid medium used to prepare the ME biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 grams per liter, preferably at least about 150 or about 200, and often between about 250 and about 750, grams per liter of the liquid medium used to make the biocatalysts.

Any suitable process may be used to solidify or polymerize the polymeric material or to adhere or fuse particles to form the open, porous polymeric matrix with microorganism irreversibly retained therein. The conditions of suitable processes should not unduly adversely affect the microorganisms. As microorganisms differ in tolerance to temperatures, pressures and the presence of other chemicals, some matrix-forming processes may be more advantageous for one type of microorganism than for another type of microorganism.

Preferably the polymeric matrix is formed from solidification of a high molecular weight material, by polymerization or by cross-linking of prepolymer in manner that a population of microorganisms is provided in the interior of the biocatalyst as it is being formed. Exemplary processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically, the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to about 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carageenan, agar, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers: monomethacrylates such as polyethylene glycol monomethacrylate, polypropylene glycol monomethacrylate, polypropylene glycol monomethacrylate, methoxydiethylene glycol methacrylate, methoxyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate; monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;
dimethacrylates such as 1,3-butylene glycol dimethacrylate, 1,4-butanediol dimethacrylate, ethylene glycol dimethacrylate, Methylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate;

amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl ethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, pyrrolidinone, 2-vinyl pyridine, 1-vinyl imidazole, 9-vinyl carbazone, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink in the broth. Typical additives include, but are not limited to, starch, glycogen, cellulose, lignin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to about 100 microns in major dimension.

If desired, the microorganisms may be subjected to stress as is known in the art. Stress may be one or more of starvation, chemical or physical conditions. Chemical stresses include toxins, antimicrobial agents, and inhibitory concentrations of compounds. In some instances, subjecting the biocatalyst to a butanol-containing liquid prior to its use as a biocatalyst can enhance the ability of the microorganisms to tolerate the presence of butanol. Often, the butanol is provided in an aqueous medium which contains at least about 2 mass percent butanol. The contact with the aqueous medium may be from about 5 or about 10 minutes to about 24 or more hours. If desired, the contact to induce the stress can be repeated. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

DRAWINGS

The processes of the invention will be further described in connection with FIGS. 1 and 2. The figures omit minor equipment such as pumps, compressors, valves, instruments and other devices the placement of which and operation thereof are well known to those practiced in chemical engineering. The figures also all omit ancillary unit operations.

One aspect of this process is further illustrated in FIG. 1 which is a schematic depiction of a bioreactor assembly 100 for the production of n-butanol. A sugar-containing feedstock is provided via line 102 to first bioreactor 104 which is an up-flow bioreactor containing an aqueous fermentation medium and biocatalyst for the bioconversion of sugar to n-butanol. The biocatalyst contains *Clostridia acetobutyricum* set forth in Example 7 below. In bioreactor 104, the supply of sugar is such that only a portion is bioconverted to butanol and thus provides an aqueous medium containing about 6 to 8 volume percent butanol, Aqueous medium from first bioreactor 104 is passed via line 106 to second bioreactor 108 where the remaining sugars are bioconverted. Second bioreactor 108 is a fluidized bed bioreactor. Second bioreactor 108 contains an aqueous medium with biocatalyst containing *Clostridia acetobutyricum* such as set forth in Example 7. In the second bioreactor, some of the remaining sugar is bioconverted to provide an aqueous medium containing about 10 volume percent butanol. Aqueous medium is withdrawn from second bioreactor 108 via line 110 and passed to decanter 114 to provide an upper phase containing n-butanol which is passed via line 116 to product recovery. The high concentration of butanol in line 116 facilitates the recovery of butanol with a substantial saving in energy costs.

A butanol-saturated aqueous phase is returned via line 118 from decanter 114 to second bioreactor 108 and contains about 7 to 8 volume percent butanol and unreacted sugars, ethanol and acetone. A purge is removed via line 120 to maintain steady-state conditions. This stream can be used for product recovery to obtain ethanol, acetone and butanol. Second bioreactor 108 can be operated such that with the recycle rate of the aqueous medium, only a portion of the sugar is bioconverted, but that converted to butanol goes to a butanol phase for recovery. If required, additional water and nutrients can be provided to first bioreactor 104 via line 122.

Figure 2:
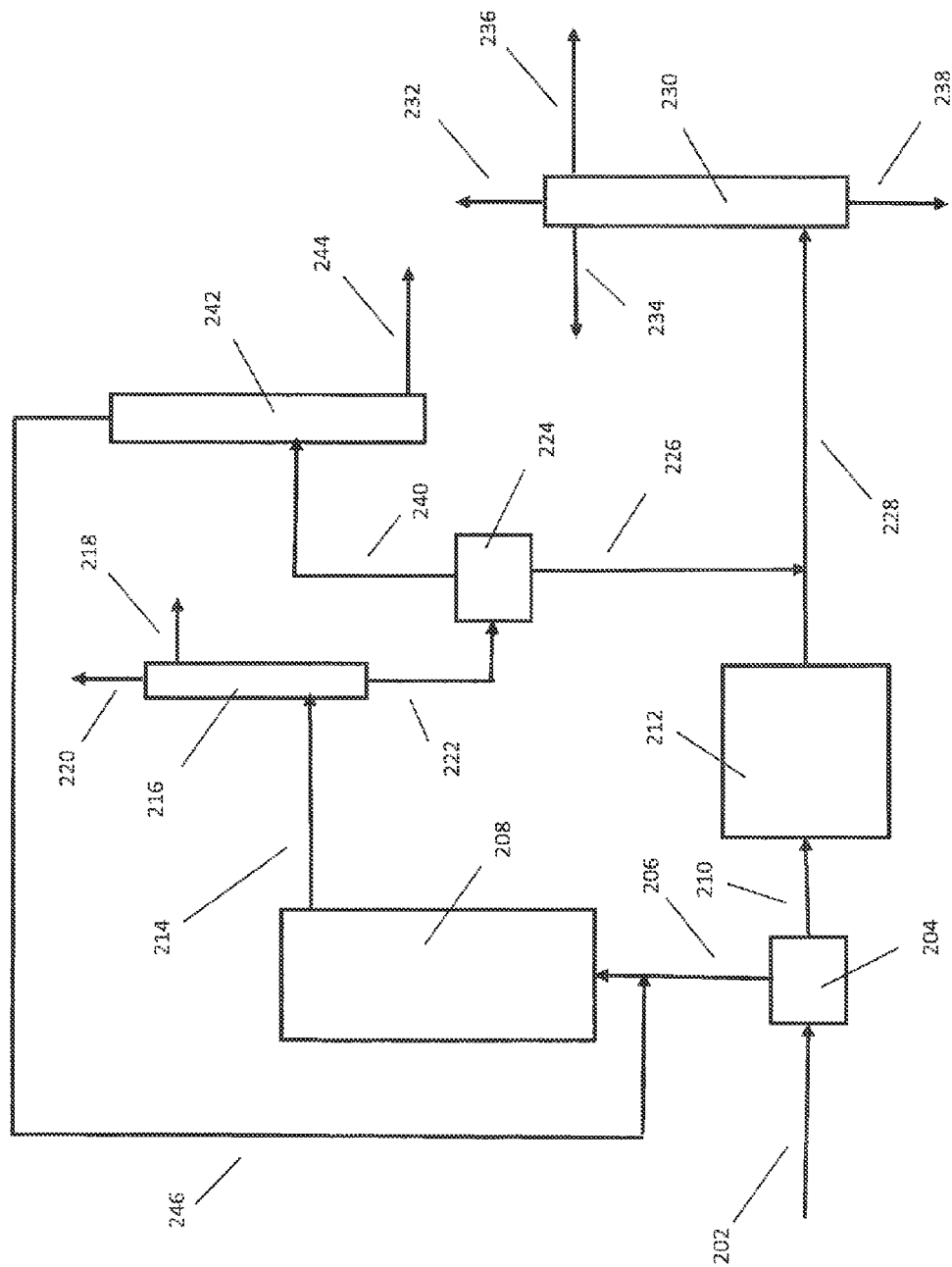
FIG. 2 is a schematic depiction of another apparatus useful in the practice of processes of this invention illustrating integration with a corn ethanol plant.

FIG. 2 is a schematic depiction of an apparatus useful in practicing the processes of this invention is integrated with a sugar ethanol process. For purposes of this illustration, the sugar is obtained from a dry milling of corn which has been subjected to hydrolysis and liquefaction. As shown, a corn sugar-containing hydrozylate is passed via line 202 to centrifuge 204 to provide a clear fraction which is passed via line 206 to bioreactor assembly 208. The clear fraction is a minor portion of the hydrozylate, for example, about 20 volume percent. The remainder of the hydrozylate is provided to fermentation assembly 212 via line 210. Fermentation assembly 212 can be a standard batch fermentation such as disclosed in U.S. patent application Ser. No. 13/918,838. The fraction to be passed to bioreactor assembly 208 can be concentrated, e.g., by evaporation of water. As discussed later, a recycle of azeotrope of butanol and water is provided to bioreactor assembly 208 and the condensate from the azeotrope can maintain sugars in solution as well as a suitable viscosity for effective contact between the substrate and biocatalyst.

Bioreactor assembly 208 comprises two fluidized bed bioreactors in flow series containing biocatalysts such as described in Example 7 and is maintained under fermentation conditions such as Typical Mesophilic Conditions. The residence time of the hydrozylate in bioreactor assembly 208 is sufficient to enable the microorganisms to consume at least about 98 percent of the $C_6$ sugars contained in the portion of the hydrozylate fed to the bioreactor assembly. Fermentation broth is withdrawn from bioreactor assembly 208 via line 214 and is passed to lights column 216. Lights column 216 serves to remove carbon dioxide, acetone, and ethanol from the fermentation broth and to assure that little, if any, acetone and ethanol are contained in the carbon dioxide effluent from the lights column. Carbon dioxide exits lights column via line 220 and an acetone-containing fraction exits via line 218. The acetone-containing fraction, due to the vapor pressure of ethanol, contains some ethanol. This acetone-containing fraction may be used for fuel, process to recover acetone, process to convert acetone to isopropanol, or otherwise disposed.

A bottoms fraction is withdrawn from lights column 216 via line 222 and is passed to decanter 224. The bottoms fraction contains a two phase mixture of water and butanol. Decanter 224 provides a lower, aqueous fraction that contains water and ethanol and about 8 percent by volume butanol. It will also contain organic acid metabolites. This aqueous fraction will also contain sugars not capable of being metabolized by the microorganisms. This aqueous fraction exits via line 226 and is combined with the fermentation broth from fermentation assembly 212 which is passed from fermentation assembly 212 via line 228 to beer still 230. Beer still 230 can be a conventional beer still used in corn ethanol plants. Beer still 230 provides a lights fraction which exits via line 232 and ethanol product which is withdrawn via line 236. Since beer still 230 is a conventional apparatus, the operations to recover fusel oil are also employed to recover the butanol passing to beer still 230 from decanter 224. The fusel oil exits via line 234. An aqueous bottoms stream exits from beer still 230 via line 238.

Alternatively, the aqueous phase from decanter 224 can be passed to a water distillation column to provide a bottoms fraction containing substantially no butanol and an overhead containing butanol/water and ethanol/water azeotropes. This overhead can be provided to lights column 216. Lights column 216 will thus serve to remove ethanol/water azeotrope and recycle butanol to decanter 224 for recovery.

A butanol-containing phase that is formed in decanter 224 is passed via line 240 to butanol column 242. An essentially pure butanol product is withdrawn from a lower portion of butanol column 242 via line 244. Since the butanol phase in decanter 224 contains dissolved water, a butanol/water azeotrope is taken as the overhead from butanol column 242 and is passed via line 246 for recycle to bioreactor assembly 208. The recycle serves to increase the butanol concentration in bioreactor assembly 208 and facilitates formation of a water-immiscible butanol phase in the bioreactor assembly.

Although the drawings depict bioconversion of sugar, it is evident that the apparatus can be used for the bioconversion of other substrates to butanol such as syngas and such as carbon dioxide via a photosynthesis and the bioconversion of substrates to other butanols such as isobutanol.

EXAMPLES

The examples are illustrations of embodiments of the invention and are not in limitation thereof. All parts and percentages of solids are by mass and of liquids and gases are by volume unless otherwise stated or evident from the context.

Examples 1 to 16

In these examples, the following general procedure is used. The microorganisms for the biocatalyst are grown under suitable planktonic conditions in an aqueous medium for the microorganisms including the presence of nutrients and micronutrients. This medium is referred to herein as the "Culture Medium". The microorganisms used are as available and thus may be either substantially pure strains or mixed cultures. The cell density in the Culture Medium is determined by optical density. If the cell density of the Culture Medium is below that sought to make the biocatalyst, the Culture Medium is centrifuged or filtered to provide a denser, cell-containing fraction. A separately prepared aqueous solution of solubilized precursor is made (referred to herein as the "Polymer Solution"). Any solid additive for the biocatalysts is added to the Polymer Solution in amounts that will provide the sought amount in the biocatalyst. The Polymer Solution is mixed with a mechanical stirrer to assure uniform dispersion of the components in the aqueous medium. Where necessary to solubilize the precursor, the Polymer Solution can be heated as appropriate. In some instances, a micronutrient solution is also added to the Polymer Solution.

Aliquots of each of the Culture Medium (or dense phase from centrifugation) and Polymer Solution are admixed under mechanical stifling at about 30° C. to for a Precursor Solution. Where the microorganism is anaerobic, the Culture Medium and the mixing of the Culture Medium and Polymer Solution and all subsequent steps are maintained under anaerobic conditions by purging with nitrogen.

The Precursor Solution is then extruded through a perforated plate having orifices of about 0.75 millimeter in diameter to form droplets of about 3 millimeters in diameter. The droplets fall into a gently stirred coagulating bath of an aqueous boric acid solution having a pH of about 5. The biocatalyst is recovered from the coagulating bath and washed with distilled water. The biocatalyst, after washing, is placed in a liquid medium containing micronutrients and the substrate under suitable metabolic conditions for the microorganisms.

Table I summarizes the examples. Table II sets forth the microorganisms used in the examples. Table III sets forth the hydrophilic polymer(s) that is used in the examples. Table IV sets forth the solid additive packages used in the examples.

TABLE I

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 1 | C | 73 | M-6 | 310 | 27 | N/A | N/A |
| 2 | CCC | 66 | M-6 | 455 | 34 | S-6 | 0.55 |
| 3 | H | 68 | M-6 | 410 | 32 | S-25 | 2.5 |
| 4 | G | 66 | M-6 | 320 | 34 | N/A | N/A |
| 5 | Q | 77 | M-5 | 560 | 23 | S-3 | 0.1 |
| 6 | B | 68 | M-5 | 480 | 32 | S-7 | 2.0 |
| 7 | H | 80 | M-5 | 600 | 20 | N/A | N/A |
| 8 | HH | 63 | M-6 | 490 | 37 | N/A | N/A |
| 9 | GG | 59 | M-5 | 95 | 41 | S-4 | 0.32 |
| 10 | E | 72 | M-5 | 360 | 28 | S-25 | 0.1 |
| 11 | LLL | 80 | M-5 | 745 | 20 | S-6 | 0.8 |
| 12 | W | 53 | M-7 | 240 | 47 | S-26 | 0.5 |
| 13 | UUU | 67 | M-5 | 580 | 33 | S-23 | 1.0 |
| 14 | S | 44 | M-6 | 250 | 56 | S-3 | 0.84 |
| 15 | Z | 60 | M-7 | 420 | 40 | N/A | N/A |
| 16 | QQ | 52 | M-7 | 250 | 48 | N/A | N/A |

TABLE II

| Microorganism Identifier | Microorganism |
|---|---|
| M-5 | *Clostridium acetobutylicum* ATCC ® 824 ™ |
| M-6 | *Clostridium pasteurianum* ATCC ® 6013 ™ |
| M-7 | *Clostridium beijerinckii* ATCC ® 10132 ™ |
| M-8 | *Clostridium butyricum* ATCC ® 19398 ™ |

TABLE III

| Polymer Solution Identifier | Composition |
|---|---|
| B | 25 wt. percent of Poly(acrylamide-co-acrylic acid) potassium salt-cross-linked available as Sigma-Aldrich 432776; 0.2 wt. percent of Poly(2-hydroxyethyl methacrylate) available as Sigma-Aldrich P3932 |
| C | 14 wt. percent of poly(vinyl alcohol-co-ethylene) available as Sigma-Aldrich 414093 having an ethylene composition of 32 mol percent; 2.0 wt. percent of polyethylene glycol with an average molecular weight of 200 available as Sigma-Aldrich P3015 |
| E | 9.5 wt. percent of polyethylene oxide available as POLYOX ™ WSR N-10 from The Dow Chemical Company having an approximate molecular weight of 100,000; 0.5 wt. percent of polyethylene glycol with an average molecular weight of 200 available as Sigma-Aldrich P3015 |
| G | 22.5 wt. percent of polyvinyl alcohol available as Elvanol ® 70-20 from E.I. duPont de Nemours having a degree of hydrolysis of 98.5-99.2 mol percent; 2.0 wt. percent of xantham gum from *Xanthamonas campestris* available as Sigma-Aldrich G1253 |
| H | 15.0 wt. percent of polyvinyl alcohol available as Mowial ® 28-99 from Kuraray Co., Ltd. having a degree of hydrolysis of 99.0-99.8 mol percent and a molecular weight of 145,000; 3.5 wt. percent of sodium alginate available as Nalgin ™ MV-120 from Ingredient Solutions, Inc. |
| Q | 13.0 wt. percent of polyethylene oxide available as POLYOX ™ WSR N-80 from The Dow Chemical Company having an approximate molecular weight of 200,000; 2.1 wt. percent polyaniline available as Sigma-Aldrich 577073 |
| S | 50.0 wt. percent of polyvinyl alcohol available as Elvanol ® 70-03 from E.I. duPont de Nemours having a degree of hydrolysis of 98-98.8 mol percent; 0.2 wt. percent polyaniline available as Sigma-Aldrich 577073 |
| W | 10.0 wt. percent of polyethylene oxide available as POLYOX ™ WSR N-80 from The Dow Chemical Company having an approximate molecular weight of 200,000; 10.0 wt. percent of polyethylene glycol with an average molecular weight of 200 available as Sigma-Aldrich P3015; 10.0 wt. percent κ-Carrageenan available as Sigma-Alrdich ® 22048 |
| Z | 20.0 wt. percent of Elvanol ® 70-04 polyvinyl alcohol from E.I. duPont de Nemours having a degree of hydrolysis of 98.0-98.8 mol percent; 1.90 wt. percent of sodium alginate available as Nalgin ™ MV-120 from Ingredient Solutions, Inc.; 1.0 wt. percent κ-Carrageenan available as Sigma-Alrdich ® 22048 |
| GG | 14.4 wt. percent of polyvinyl alcohol available as Elvanol ® 70-14 from E.I. duPont de Nemours Inc. having a degree of hydrolysis of 95.0-97.0 mol percent; 14.0 wt. percent of polyacrylic acid with an average molecular weight of 1800 available as Sigma-Aldrich 323667 |
| HH | 18.1 wt. percent of poly(vinyl alcohol-co-ethylene) available as Sigma-Aldrich 414093 having an ethylene composition of 32 mol percent; 5.5 wt. percent of Poly(2-hydroxyethyl methacrylate) available as Sigma-Aldrich P3932; 1.0 wt. percent of anhydrous calcium chloride available as Sigma-Aldrich C1016 |
| QQ | 40.0 wt. percent of polyvinyl alcohol available as Poval ® PVA-224E from Kuraray Co., Ltd. having a degree of hydrolysis of 80-83 mol percent; 0.7 wt. percent of medium molecular weight Poly(D-glucosamine) available as Sigma-Aldrich 448877 |

TABLE III-continued

| Polymer Solution Identifier | Composition |
|---|---|
| CCC | 17.0 wt. percent of polyvinyl alcohol available as Sigma-Aldrich 363138 having a degree of hydrolysis of 98-99 mol percent and a molecular weight of 31,000-50,000; 3,0 wt. percent of ethylene glycol dimethacrylate available as Sigma-Aldrich 335681 |
| LLL | 3.5 wt. percent of polyethylene-alt-maleic anhydride available as Sigma-Aldrich 188050 having an average molecular weight 100,000-500,000; 1.0 wt. percent of ethylene glycol dimethacrylate available as Sigma-Aldrich 335681; 0.05 wt. percent of anhydrous calcium chloride available as Sigma-Aldrich C1016 |
| UUU | 9.0 wt. percent of poly(N-isopropylacrylamide) available as Sigma-Aldrich 535311 having a molecular weight of 19,000-30,000; 1.1 wt. percent of sodium alginate available as Nalgin ™ MV-120 from Ingredient Solutions, Inc. |
| VVV | 10.5 wt. percent of ethylene vinyl alcohol copolymer available as Exceval ™ RS-1717 from Kuraray Co., Ltd. having a degree of hydrolysis of 92-94 mol percent; 2.2 wt. percent of Poly(2-hydroxyethyl methacrylate) available as Sigma-Aldrich P3932 |
| WWW | 10.0 wt. percent of polyvinyl alcohol available as Mowial ® 28.99 from Kuraray Co., Ltd. having a degree of hydrolysis of 99.0-99.8 mol percent and a molecular weight of 145,000; 4.5 wt. percent of medium molecular weight Poly(D-glucosamine) available as Sigma-Aldrich 448877 |
| XXX | 10.0 wt. percent of poly(vinyl alcohol-co-ethylene) available as Sigma-Aldrich 414093 having an ethylene composition of 32 mol percent; 2.0 wt. percent of xantham gum from *Xanthamonas campestris* available as Sigma-Aldrich G1253 |

TABLE IV

| Solid Additive Package Identifier | Composition |
|---|---|
| S-3 | Clay available as Nanomer ® I.44P from Sigma-Aldrich 682624 containing 35-45% wt. % dimethyl dialkyl amine on Montmorillonite clay base material matrix |
| S-4 | Clay available as Nanomer ® I.34MN from Sigma-Aldrich 682640 containing 25-30 wt. % methyl dihydroxyethyl hydrogenated tallow ammonium on Montmorillonite clay base material matrix |
| S-6 | Natural bentonite clay as Cloisite ® 116 from Southern Clay Products/Rockwood Additives |
| S-7 | Granular activated carbon having an effective size 0.7-0.9 mm available as HYDRODARCO ® 3000 from Norit Americas |
| S-23 | Chitin as available as Sigma-Aldrich C7170 |
| S-25 | Fine ground silica available as MIN-U-SIL ® from U.S. Silica |
| S-26 | Polyethylene powder as MIPELON ™ from Mitsui Chemicals America, Inc. |

Each of the above biocatalysts exhibit phenotypic alterations and the biocatalysts have a stable population of microorganisms and do not generate any appreciable debris from metabolic activity.

Examples 17 to 23

A series of seven batch fermentation experiments are conducted using the following general procedure. In each experiment, a biocatalyst substantially as described in Example 7 is used which has a nominal diameter of about 4 millimeters and is maintained under an anaerobic environment of nitrogen. A batch medium is prepared in accordance with ATCC® Medium 2107, a modified reinforced Clostridial agar/broth medium, as follows:

Combine 38 grams of reinforced clostridial medium BD 218081 (ATCC, Manassas, Va.); 14.5 g of agar and 1000 milliliters of deionized water and boil to dissolve the agar, Separately prepare a solution of 10 grams of peptone, 10 grams of beef extract, 3 grams of yeast extract, 5 grams of dextrose, 5 grams of sodium chloride, 1 gram of soluble starch, 0.5 gram of L-cysteine hydrochloride, 3 grams of sodium acetate and 4 milliliters of Resazurin (0.025%) in 1000 milliliters of deionized water, and Combine the solutions.

Glucose is added to the combined solution at either 60 or 120 grams per liter, and the solution is adjusted to a pH of about 5.5 with 5N sodium hydroxide. The batch medium is then made anaerobic by autoclaving at 121° C. for 20 minutes while sparging with nitrogen that had been passed through a 0.2 micron filer. Each batch fermentation is conducted in a sealed tank reactor and about 2 milliliters of the batch medium is used per gram of biocatalyst. Into some of the reactors, n-butanol is injected to determine the effect of n-butanol on the biocatalysts and the fermentation. The fermentations are conducted at a temperature of about 37° C., and samples of the fermentation broth are taken periodically and analyzed by gas chromatography. The fermentations continue for 48 hours. The data are summarized in Table IV.

TABLE IV

| Example | Glucose added, g/L | n-Butanol added, vol % | Comments |
|---|---|---|---|
| 17 | 120 | 0 | Butanol being produced |
| 18 | 120 | 2 | Butanol being produced |
| 19 | 120 | 5 | Butanol being produced |
| 20 | 120 | 10 | Butanol being produced at reduced rate, two phases in broth |
| 21 | 60 | 10 | Butanal being produced at reduced rate, two phases in broth |
| 22 | 120 | 15 | Butanol being produced at reduced rate, two phases in broth |
| 23 | 120 | 22 | Butanol being produced at reduced rate, two phases in broth |

In each of the above examples 17 to 23, sugar is consumed. An analysis by gas chromatography of the aqueous phase in each of the above experiments is conducted. The analyses detect the presence of lactic acid, acetic acid, and acetone. Table V summarizes the analyses in the aqueous phase:

TABLE V

| Example | Lactic acid, g/L | Acetate, g/L | Ethanol, g/L | Acetone, g/L |
|---|---|---|---|---|
| 17 | 4.8 | 2.0 | 1.8 | 0.6 |
| 18 | 4.9 | 1.9 | 2.0 | 0.6 |
| 19 | 1.5 | 1.0 | 0.1 | 0.7 |
| 22 | 1.2 | 0.7 | 0.1 | 0.5 |
| 23 | 1.3 | 0.8 | 0.1 | 0.4 |

It is claimed:

1. A process for the bioconversion of substrate to bioproduct comprising butanol with a biocatalyst comprising microorganisms capable of bioconverting said substrate to butanol, said process comprising:
   a. contacting said substrate with said biocatalyst under metabolic conditions for a time sufficient to bioconvert at least a portion of said substrate to butanol, and
   b. recovering butanol, wherein said biocatalyst comprises microorganisms substantially irreversibly retained in a solid structure, said a solid structure being composed of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more wherein said microorganisms have a population in the interior structure of about 60 grams per liter or more based upon the volume defined by the exterior of the solid structure when fully hydrated, wherein the microorganisms maintain their population substantially stable.

2. The process of claim 1, wherein said contacting is in an aqueous medium and butanol is recovered from said aqueous medium.

3. The process of claim 2, wherein the butanol forms a separate liquid phase in a bioreactor assembly.

4. The process of claim 2, wherein the butanol is isobutanol or n-butanol.

5. The process of claim 2, wherein the substrate comprises sugar.

6. The process of claim 1, wherein the HEV of the solid structure is about 5000 or more and the solid structure forms an external skin.

7. The process of claim 5, wherein about 40 to 70 percent of the volume of the biocatalyst comprises said major cavities and the biocatalyst contains smaller cavities, wherein said smaller cavities have a maximum cross-sectional diameter of up to 5 microns.

8. The process of claim 5, wherein the HEV of the solid structure is about 20,000 or more and the concentration of microorganisms in the interior of the solid structure is about 100 grams per liter or more based upon the volume defined by the exterior of the solid structure.

9. The process of claim 5, wherein the biocatalyst contains an exo-network of said microorganisms.

10. The process of claim 5, wherein the microorganism population is a single strain-type.

11. The process of claim 1, wherein the process is continuous.

12. The process of claim 11, wherein the microorganism is C. acetobutylicum, C. beijerinckii, C. pasteurianum, C. saccharobutylicum, C. saccharoperbutylacetonicum; Oeneococcus oeni; Ralstonia eutropha, or recombinant E. coli or Saccharomyces cerevisiae into which pathways for making butanol have been added.

13. The process of claim 1, wherein the substrate comprises at least one of carbon monoxide and a mixture of hydrogen and carbon dioxide.

14. A process of claim 1, wherein the microorganism population exhibits a phenotypic change enhancing tolerance of the biocatalyst to butanol.

15. A continuous process for the bioconversion of substrate to bioproduct comprising butanol with a biocatalyst comprising microorganisms capable of bioconverting said substrate to butanol, said process comprising:
   a. continuously supplying said substrate to a bioreactor assembly containing an aqueous medium and biocatalyst;
   b. contacting said substrate with said biocatalyst in an aqueous medium under metabolic conditions for a time sufficient to bioconvert at least a portion of said substrate to butanol to provide a butanol-laden liquid medium,
   c. withdrawing continuously or intermittently a portion of the butanol-laden liquid medium from the bioreactor assembly; and
   d. recovering butanol from said butanol-laden liquid medium, wherein said biocatalyst comprises microorganisms substantially irreversibly retained in a solid structure, said a solid structure being composed of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more wherein said microorganisms have a population in the interior structure of about 60 grams per liter or more based upon the volume defined by the exterior of the solid structure when fully hydrated, wherein the microorganisms maintain a their population substantially stable.

16. The process of claim 15, wherein butanol is recovered from said butanol-laden liquid medium by (i) phase separating to provide a butanol phase and an aqueous phase; (ii) fractionating by distillation said butanol phase to provide a bottoms fraction comprising butanol and a lower-boiling fraction comprising azeotrope of butanol and water; and (iii) passing to said bioreactor assembly at least a portion of the lower-boiling fraction such that a butanol-containing phase exists in the bioreactor assembly, wherein said butanol-laden medium contains two phases.

17. The process of claim 16, wherein the butanol is at least one of isobutanol and n-butanol.

18. The process of claim 16, wherein the process for making butanol is integrated with a process for bioconverting sugar to ethanol, and at least a portion of the aqueous phase separated in step (i) passes to the process for bioconverting sugar to ethanol for fractionation by distillation.

19. The process of claim 16, wherein the substrate comprises at least one of carbon monoxide and a mixture of hydrogen and carbon dioxide.

20. A process for the bioconversion of substrate to butanol using a microorganism capable of such bioconversion wherein butanol is toxic to the microorganism comprising:
   a. continuously supplying substrate and aqueous medium to at least one first bioreactor containing aqueous medium, said at least one first bioreactor having therein a biocatalyst, wherein said biocatalyst comprises microorganisms substantially irreversibly retained in a solid structure, said a solid structure being composed of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more wherein said microorganisms have a population in the interior structure of about 60 grams per liter or more based upon the volume defined by the exterior of the solid structure when fully hydrated, wherein the microorganisms maintain a their population substantially stable;
   b. maintaining said at least one first bioreactor under metabolic conditions and continuously withdrawing a first reactor effluent from said at least one first bioreactor at a rate sufficient to maintain steady-state conditions and provide a hydraulic residence time sufficient to bioconvert a portion of the substrate, said a first bioreactor effluent containing unconsumed substrate and butanol, wherein the bioconversion activity to butanol in said at least one first bioreactor is at a first rate;

c. continuously supplying the withdrawn first bioreactor effluent to at least one subsequent bioreactor containing aqueous medium, said at least one subsequent bioreactor having therein biocatalyst, wherein said biocatalyst comprises microorganisms substantially irreversibly retained in a solid structure, said a solid structure being composed of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more wherein said microorganisms have a population in the interior structure of about 60 grams per liter or more based upon the volume defined by the exterior of the solid structure when fully hydrated, wherein the microorganisms maintain a their population substantially stable;

d. maintaining said at least one subsequent bioreactor under metabolic conditions and continuously withdrawing a subsequent bioreactor effluent from said at least one subsequent bioreactor at a rate sufficient to maintain steady-state conditions and provide a hydraulic residence time sufficient to bioconvert at least a portion of the substrate, said a subsequent bioreactor effluent containing butanol, wherein the bioconversion activity to said butanol in said at least one subsequent bioreactor is at a second rate which is lower than the first rate;

e. continuously separating a butanol-rich stream from said withdrawn subsequent bioreactor effluent for product recovery and to provide a residual aqueous stream; and f. continuously recycling at least a portion of the residual aqueous stream to at least one subsequent bioreactor.

21. A process for bioconverting substrate to bioproduct comprising butanol with a biocatalyst comprising microorganisms capable of bioconverting said substrate to butanol said microorganism being capable of producing other metabolites, comprise:

a. contacting said biocatalyst with butanol in a concentration sufficient to alter the ratio of butanol production to the production of other metabolites in favor of the production of butanol;

b. contacting said substrate with said biocatalyst under metabolic conditions for a time sufficient to bioconvert at least a portion of said substrate to butanol, and c. recovering butanol, wherein said biocatalyst comprises microorganisms substantially irreversibly retained in a solid structure, said a solid structure being composed of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more wherein said microorganisms have a population in the interior structure of about 60 grams per liter or more based upon the volume defined by the exterior of the solid structure when fully hydrated, wherein the microorganisms maintain a their population substantially stable.

22. The process of claim 21, wherein step (a) is preferably conducted by contacting the biocatalyst with an aqueous solution containing butanol.

23. The process of claim 21, the aqueous solution contains a concentration of about 5 or more, mass percent butanol.

24. The process of claim 23, wherein steps (a) and (b) occur at the same time.

25. The process of claim 21, wherein the process is continuous and a portion of the butanol withdrawn from a bioreactor assembly used in the processes, is recycled to the bioreactor.

* * * * *